United States Patent [19]

Wigness et al.

[11] Patent Number: 4,705,501
[45] Date of Patent: Nov. 10, 1987

[54] BI-DIRECTIONAL, ANTI-REFLUX VASCULAR ACCESS SYSTEM

[75] Inventors: Bruce D. Wigness; Michael H. Anderson, both of Minneapolis, Minn.

[73] Assignee: Regents of the University of Minnesota, Minneapolis, Minn.

[21] Appl. No.: 367,683

[22] Filed: Apr. 12, 1982

[51] Int. Cl.⁴ .............................................. A61M 25/00
[52] U.S. Cl. ...................................... 604/43; 604/175; 604/256; 604/283
[58] Field of Search ...................................... 604/27–30, 604/34, 43, 96–103, 175, 256, 283

[56] References Cited

U.S. PATENT DOCUMENTS

| | | | |
|---|---|---|---|
| 3,331,371 | 7/1967 | Rocchi et al. | 604/96 |
| 3,552,441 | 1/1971 | Luhleich | 604/86 X |
| 3,730,170 | 5/1973 | Michael | 604/86 X |
| 4,160,454 | 7/1979 | Foux | 604/175 X |
| 4,240,433 | 12/1980 | Bordow | 604/96 X |
| 4,248,234 | 2/1981 | Assenza et al. | 604/256 X |
| 4,301,797 | 11/1981 | Pollack | 604/256 X |

Primary Examiner—Dalton L. Truluck
Attorney, Agent, or Firm—Burd, Bartz & Gutenkauf

[57] ABSTRACT

An implantable access system for infusion of liquids into a body or aspiration of liquid samples from the body. The system includes a septum/manifold (16) and catheter (10) connected thereto, both of specific design. The septum/manifold includes a pair of manifold chambers (24, 25) each closed with a self-sealing septum (20, 22) and each having a first access entry (19) and second access entry (26, 27) (35, 36). The catheter includes a pair of concentric inner and outer tubes (11, 12). The inner tube (11) is collapsible and closed at its distal end. The outer tube (12) closely engages the inner tube and defines a catheter lumen (28) therewith when the inner tube is collapsed by evacuation. The inner and outer tubes are joined together longitudinally over a small portion of the circumference of the inner tube.

10 Claims, 12 Drawing Figures

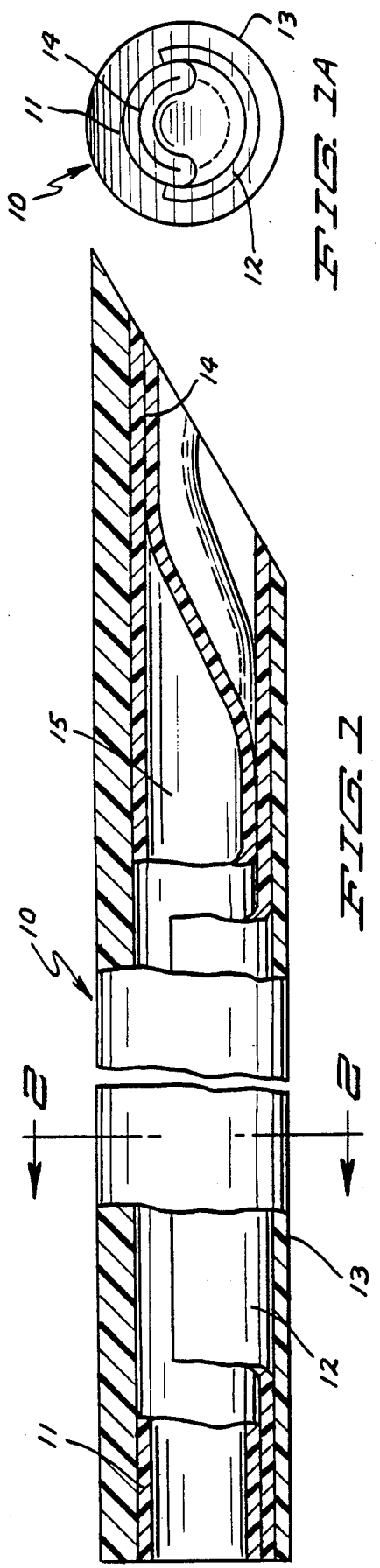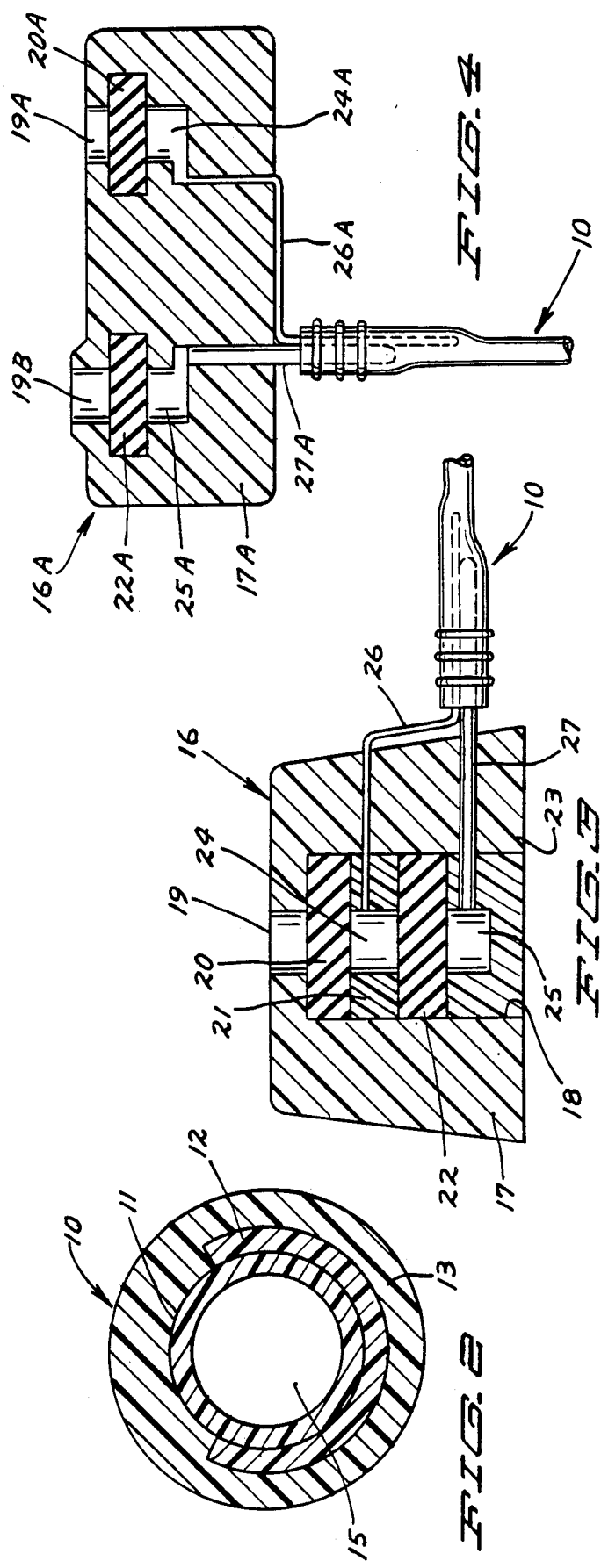

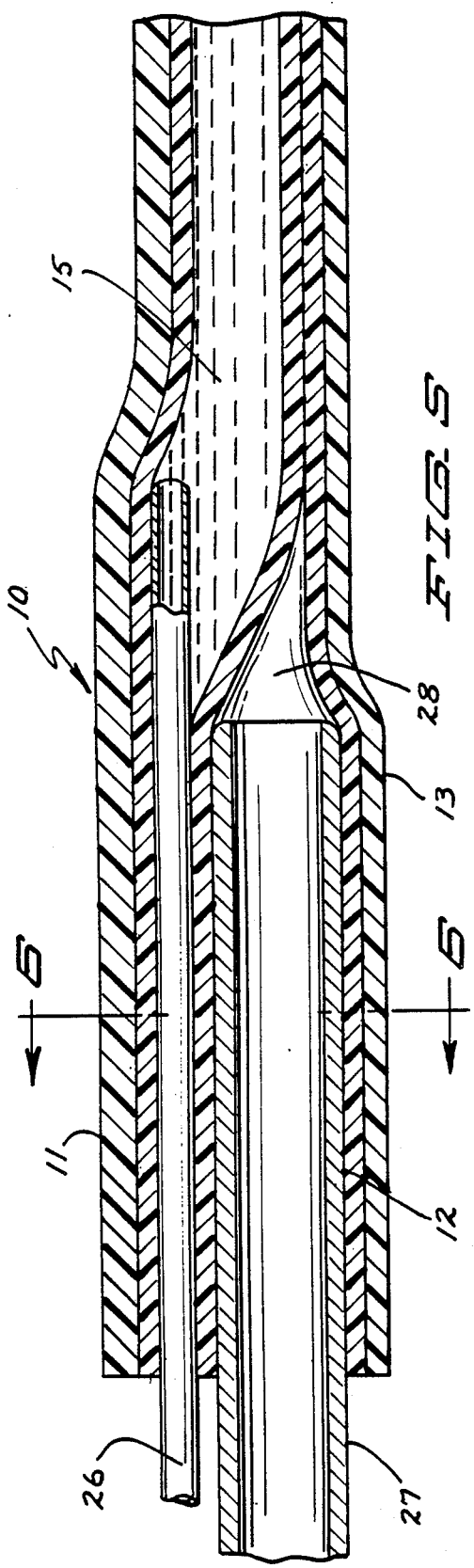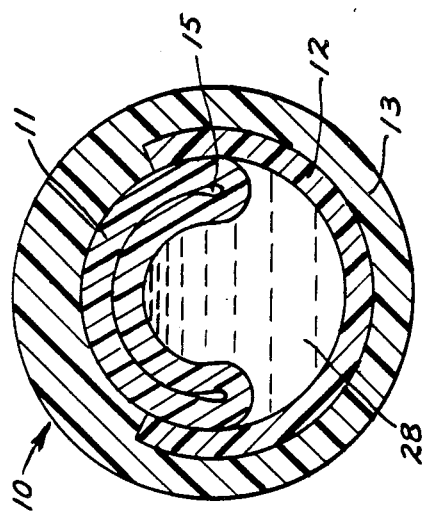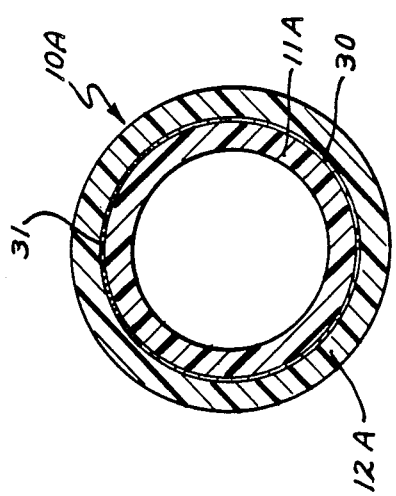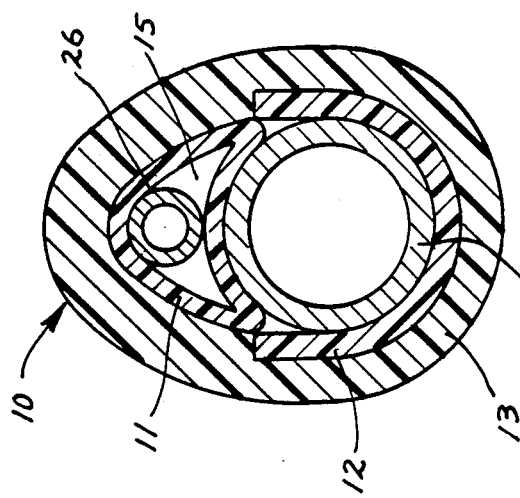

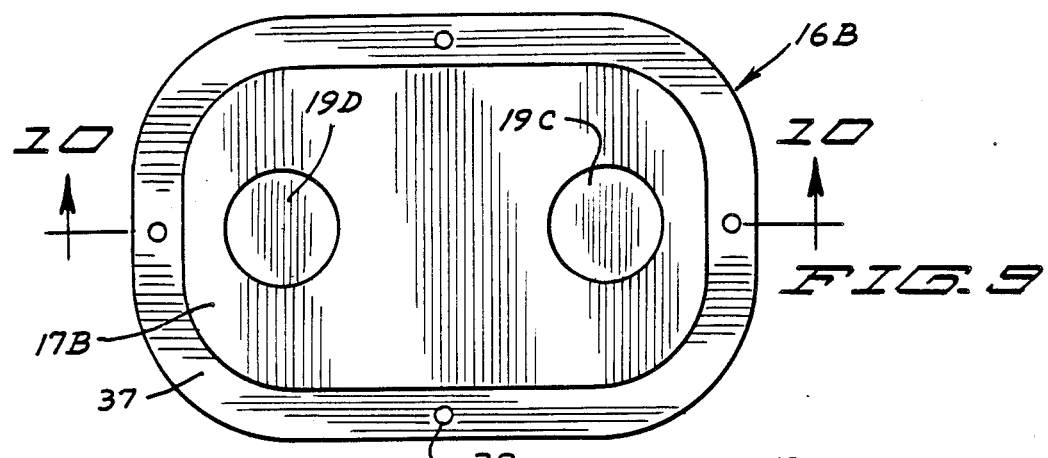
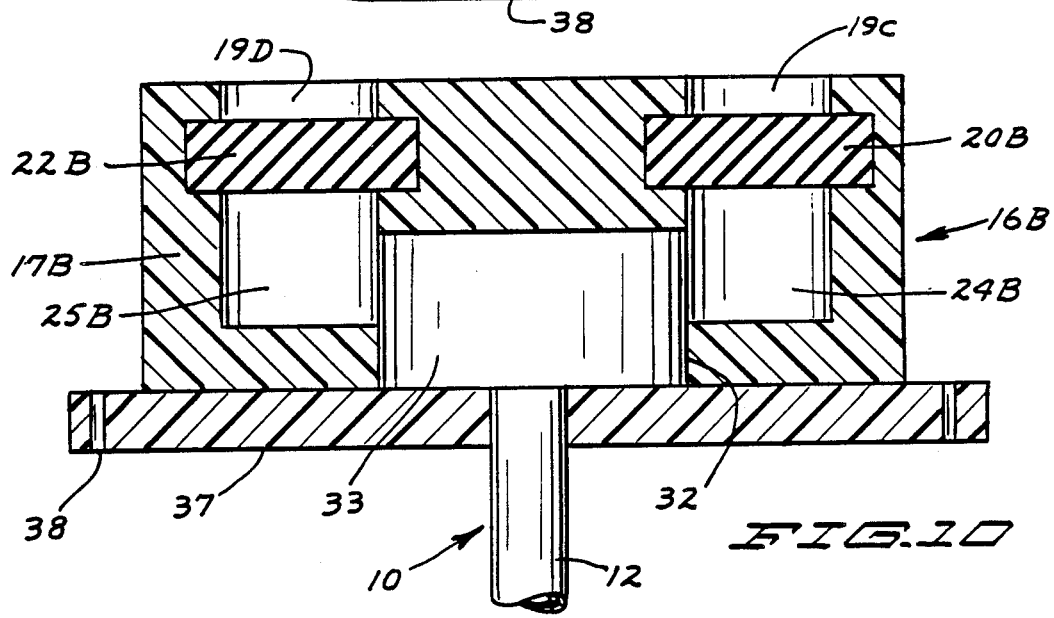
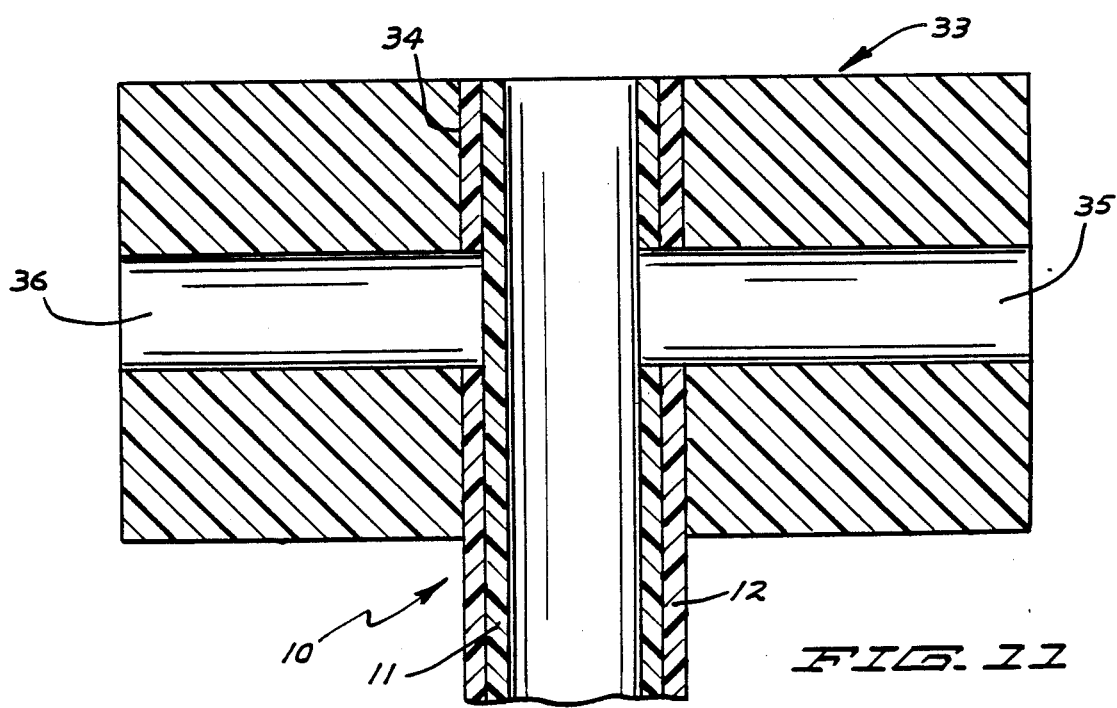

BI-DIRECTIONAL, ANTI-REFLUX VASCULAR ACCESS SYSTEM

FIELD OF THE INVENTION

1. Background of the Inventon:

This invention relates to a bi-directional, anti-reflux vascular access system comprised of a totally implantable intravascular catheter and septum/manifold. The catheter provides an access for either drug infusion or blood sampling. It is designed to prevent plugging by blood components during long periods of dormancy. This is accomplished by constructing the catheter lumen so that it can be shifted into either a "dormant" or an "active" configuration. Total implantability is achieved by attaching this catheter to a specially designed bichambered septum/manifold assembly.

Vascular catheters are commonly used in medicine and occasionally used in animal research. Applications for these catheters include infusion of parenteral fluids, single-needle hemodialysis and repeated arterial and venous blood sample collection.

2. The Prior Art:

Of the currently available intravascular catheters, the most commonly used type is made up of a plastic or rubber tube with a hub for syringe connection at one end. Implantation of these catheters results in the hub end being on the outside of the body with the rubber or plastic tube passing transcutaneously into the subcutaneous tissue and then into the blood vessel. When these catheters are not being used, the lumen is filled with a sterile solution (sometimes containing an anti-coagulant, e.g. heparinized saline) and a plug is placed in the hub. The routine daily care that is required of these catheters includes flushing the lumen with sterile solutions in order to prevent plugging with blood clots, and scrupulous cleaning of the skin in the area around the catheter-skin interface in order to avoid infection. In using these catheters in research involving experimental animals, the additional complication frequently arises of an animal removing or severing the catheters, making this work very difficult.

A more recent catheter design is one in which the rubber tube is connected to and communicates with an implantable plenum containing a septum. At the time of canulation, this type of catheter is completely implanted with the septum lying directly under the surface of the skin. In order to infuse solutions through these catheters, a hypodermic needle is pierced through the skin and septum and into the plenum. Then, a syringe filled with the solution to be infused is connected to the hub of the needle and injected. Although this type of catheter does not require daily care for the prevention of infection, the lumen can very easily become plugged with blood clots which are subsequently flushed into the cardiovascular system. This type of catheter is not useful in situations requiring aspiration of blood since the diameter of the lumen is kept small in order to minimize the diffusion of blood components. This reduces the probability of the catheter becoming irreversibly plugged by a clot too large to dislodge and furthermore minimizes the size of the thromboemboli.

A form of long term implantable catheter having a check valve tip for unidirectional flow, designed to prevent plugging of the lumen with particulates, is disclosed in a co-pending Dorman application Ser. No. 245,379, filed Mar. 19, 1981, of common ownership with the present application.

The catheter according to the present invention is also designed to avoid the hazards and inconvenience common to using the catheters currently available. By mounting the catheter tube to an implantable septum, the risk of septicemia is greatly reduced and the need for daily care is eliminated. The possibility of blood clotting in the catheter lumen during periods of dormancy is eliminated by designing the lumen so that it has both an open and a closed mode.

SUMMARY OF THE INVENTION

Broadly stated, the bi-directional, anti-reflux vascular access system according to the present invention comprises a dual-chambered implantable septum/manifold and implantable catheter connected thereto. The septum/manifold includes a housing enclosing a pair of manifold chambers. First entry means are provided to the chambers. A self-sealing septum closes the first entry means to each of the chambers. Separate second entry means are also provided to each of the chambers for connection to the catheter.

The catheter includes inner and outer generally concentric flexible tubes of substantially the same length. The inner tube is collapsible and closed at the distal or downstream end. The outer tube is open at both ends and embraces the outer wall of the inner tube. The inside wall of the outer tube normally engages the outside wall of the inner tube in a separable non-adherent relationship over a substantial (e.g. about 50 to 95%) portion of the circumference of the inner tube. This forms a normally closed passage between the tubes when the catheter is in a dormant or at rest state. The inner and outer tubes are joined together longitudinally over a small portion (e.g. about 5% or more) of the circumference of the inner tube.

The proximal or upstream end of the inner closed-end collapsible tube is connected to one of the chambers of the septum/manifold through which suction may be applied to collapse the inner tube and open the normally closed passage between the inner and outer tubes. That normally closed passage is connected to the other chamber of the septum/manifold through which liquid may be infused into the blood stream or blood may be aspirated.

The chambers of the septum/manifold may be disposed in vertically stacked relation sharing a common first entry means and separated by one of the septa. Alternatively, the chambers may be disposed in closely spaced apart side-be-side relation with separate spaced apart first entry means and septa. In its simplest form the catheter may be in the form of concentric tubes tightly fitted together and longitudinally bonded along a narrow stripe.

BRIEF DESCRIPTION OF THE DRAWINGS

The invention is illustrated in the accompanying drawings in which corresponding parts are identified by the same numerals and in which:

FIG. 1 is an elevation, partly in section to show details of construction, of an intra-vascular catheter forming part of the access system of the present invention;

FIG. 1A is a distal end view of the catheter.

FIG. 2 is a transverse section on the line 2—2 of FIG. 1 and in the direction of the arrows, showing the catheter in its dormant state;

FIG. 3 is an elevation in section of one form of septum/manifold forming part of the access system of the invention;

FIG. 4 is an elevation in section of another form of septum/manifold;

FIG. 5 is a fragmentary elevation in section, on an enlarged scale, showing the connection between catheter and septum/manifold;

FIG. 6 is a transverse section on line 6—6 of FIG. 5 and in the direction of the arrows;

FIG. 7 is a transverse section, similar to FIG. 2, through the catheter in its active state;

FIG. 8 is a transverse section, similar to FIG. 2, showing an alternative form of catheter;

FIG. 9 is a top plan view of a further alternative form of septum/manifold;

FIG. 10 is a section on the line 10—10 of FIG. 9 and in the direction of the arrows, and FIG. 11 is a longitudinal section on an enlarged scale of the connection between catheter and septum/manifold.

DETAILED DESCRIPTION OF THE PREFERRED EMBODIMENTS

Referring now to the drawings, and particularly to FIGS. 1 and 2, there is shown one form of catheter according to the present invention. The catheter, indicated generally at 10, may be of any desired length appropriate to the particular use to which it is to be put. The catheter comprises a central inner tube 11 of circular cross-section formed from any of a large number of flexible, inert, non-toxic, bio-compatible rubber or synthetic rubber-like materials. A preferred material is medical grade silicone rubber tubing. The inner tube 11 is at least partially surrounded by a closely fitting outer tube 12 preferably of the same material and of substantially the same length as the inner tube. The inside wall surface of outer tube 12 engages the outside wall surface of inner tube 11 in face-to-face contact but in a non-adherent relationshsip over most (e.g. 50 to 95%) of the circumference of the inner tube. In the embodiment shown, the outer tube 12 is slit along its entire length and about one third of its circumference is removed. Then the slitted outer tube 12 is slipped over the intact tube and is permanently mated into place by dipping or lathing on a thin layer 13 of an adhesive coating material, such as silicone rubber adhesive. This sealing coat or layer 13 fills the space between the split edges of the outer tube 12 and bonds the inner and outer tubes together along those edges. This leaves the tubes unbonded over about two thirds of the circumference of the inner tube. As explained in detail hereinafter, in use the inner tube of the catheter is collapsed and the space between the inner and outer tubes becomes the lumen of the catheter.

After assembly of the inner and outer tubes, the distal or downstream end of the inner tube 11 is pinched down and permanently laminated to itself over a distance of about ½ inch (1.27 cm) at 14. This forms a blind chamber 15 within the inner tube. The tip of the catheter is cut off at an oblique angle with the laminated side forming the distal-most edge of the bevel. As shown in FIG. 1A, the laminated end of the inner tube assumes a dimple-like configuration, as is assumed by the inner tube upon evacuation, as hereinafter explained.

Referring now to FIG. 3 there is shown one form of septum/manifold subassembly, indicated generally at 16. The septum/manifold is intended for implantation under the skin. It includes a housing 17 having a central cylindrical passage 18 in its lower portion and a connecting central passage 19 of smaller diameter through its top wall. A first self-sealing septum 20 is seated in passage 18 immediately adjacent to passage 19. A tightly fitting collar 21 is seated on septum 20. A second septum 22 is seated upon collar 21 and a cup-like needle stop plug 23 is seated upon the second septum. Housing 17, collar 21 and plug 23 are formed from a rigid inert, non-toxic, biocompatible, millable material. Polycarbonate and polyether sulfane are exemplary of such materials. The septa 20 and 22 are preferably silicone rubber. The assembled stacked septum/manifold is clamped together and the parts are fused together, i.e., polycarbonate parts with methylene dichloride.

The space between septa 20 and 22 forms a first manifold chamber 24 and the space within cup-like plug 23 forms a second manifold chamber 25. Passage 19 provides a first common access entry to both manifold chambers for a hypodermic needle or the like. Access to the manifold chambers is achieved by drilling two parallel holes perpendicular to the axis of symmetry. Two tightly fitting stainless steel tubes 26 and 27 are inserted into the appropriate holes and then bonded with methylene dichloride. Tubes 26 and 27 thus provide separate second access entries to the manifold chambers. The smaller steel tube 26 is then bent in two places so that in its final configuration it is parallel to and snug against the larger steel tube 27.

An alternative form of septum/manifold 16A is shown in FIG. 4. Manifold chambers 24A and 25A are formed in housing 17A disposed in closely spaced side-by-side relation. The chambers are closed by means of septa 20A and 22A, respectively. Separate first access entries 19A and 19B are provided to the respective chambers and separate second access entries in the form of tubes 26A and 27A are provided.

As shown in FIGS. 5 and 6, the two subassemblies are connected together as follows: The proximal end of the catheter tube 10 is attached to the septum/manifold 16 by inserting the small diameter steel tube 26 into the inner silicone rubber tube 11 (the blind chamber 15) and inserting the larger diameter steel tube 27 in between the two concentric silicone rubber tubes 11 and 12 (the catheter lumen). This joint may be wrapped with silk suture and bonded with silicone rubber adhesive.

An alternative form of catheter 10A is shown in FIG. 8. The inner tube 11A is performed. The outer surface of inner tube 11A is coated over about 50 to 95% of its circumference with a thin layer 30 of non-stick or non-adherent material relative to the material of which the catheter tubes are formed. For example, a thin layer of tetrafluoroethylene (Teflon) is applied to the outer wall of silicone rubber tubing. A one molecule thick layer may be applied as, for example, by plasma coating techniques. The partially coated tubing is dipped in silicone rubber to form an outer tube 12A surrounding the inner tube but non-adherent thereto over the coated area. A bond 31 is formed between the inner and outer tubes over the uncoated area. The inner tube 11A may be collapsed by suction forming a lumen between the inner and outer tubes. While the inner and outer tubes should be bonded along their lengths to prevent "snaking" of the inner tube which might block the lumen, this bonding need not be continuous.

A further alternative form of septum/manifold 16B is shown in FIGS. 9 through 11. Manifold chambers 24B and 25B are formed in housing 17B disposed in closely spaced side-by-side relation. The chambers are closed by means of septa 20B and 22B, respectively. Separate first access entries 19C and 19D are provided to the respective chambers. Separate second access entries are provided as follows. A chamber 32 is provided in the bottom of housing 17B communicating with chambers 24B and 25B. An insert 33 of the same size and geometrical configuration as chamber 32 is provided at the proximal end of the catheter. The insert is desireably formed of the same material and integral with the catheter, i.e., silicone rubber.

Insert 33 has a central passage 34 into which the end of the catheter is fitted and sealed. A radial passage 35 extends through the insert body and through the walls of inner and outer catheter tubes 11 and 12 to connect the blind chamber 15 with septum/manifold chamber 24B. A further diametrically opposite radial passage 36 extends through the insert body and through the wall of the outer catheter tube only, to connect the catheter lumen (28, FIG. 7) with septum/manifold chamber 25B. The insert 33 is held in place by a base plate 37 secured to the housing 17B. The base plate is desireably provided with suture holes 38 for securing the septum/manifold when implanted.

IMPLANTATION

The vascular access system is implanted using standard surgical techniques. Proper installation results in the catheter being threaded into the desired blood vessel and the manifold being secured in the subcutaneous tissue with the septa facing the skin. After implantation, the vascular access is maintained in the dormant state as shown in FIG. 2 in which the blind chamber 15 is filled with a fluid (usually normal saline, although a radio-opaque dye and air have also been used). The catheter lumen, the space between the inner and outer tubes, is closed.

OPERATIONS

There are three general operational steps involved in the use of the access system. First the partition formed by the collapsible portion of the wall of inner tube 11 or 11A is shifted from the dormant to the active state, as shown in FIG. 7, opening the lumen 28 for passage of liquid. Second, either the aspiration or infusion operation is carried out. Finally the partition is shifted back to the dormant state.

In order to shift the partition from the dormant to the active state, a needle attached to a syringe is inserted through the septum 20, 20A or 20B and into the plenum 24, 24A or 24B which communicates through steel tube 26 or 26A or passage 35 with the blind chamber 15 of the catheter. The fluid is then aspirated from the blind chamber and into the syringe. Evacuation of the blind chamber causes the partition to move towards the common wall of the catheter and consequently opens the lumen 28 of the catheter.

Next, an appropriately sized syringe attached to an appropriately sized needle is inserted through the septum 22, 22A or 22B and into the plenum 25, 25A or 25B which communicates through steel tube 27 or 27A or passage 36 with the catheter lumen 28 and either sample aspiration or infusion may be performed.

Following each use of this vascular access system it is important that the catheter lumen is flushed of any blood components. Towards the end of the catheter flushing procedure the partition is simultaneously shifted to the dormant position by slowly filling the blind chamber with a volume of fluid equivalent to that which was previously aspirated during the activation step. This volume is such that it completely displaces the lumen of the catheter by shifting the partition away from the common wall so that in its final position it seals tightly against the opposite wall. FIGS. 2 and 7 show the two configurations of the partition.

The catheter tube may have widely varying dimensions dependent upon the particular application to which it is to be put. In one exemplary catheter the inner tube 11 and outer tube 12 were constructed from two identical silicone rubber tubes with inner diameters of 0.058 inches (0.147 cm) and outer diameters of 0.077 inches (0.196 cm) for a wall thickness of 0.0095 inches (0.024 cm). The initial length of these tubes is about 1 to 2 inches (2.54 to 5 cm) longer than the final desired length. The sealing coating or layer 13 is about 0.015 inch (0.038 cm). The smaller steel tube 26 is 25 gauge, about 0.02 inch (0.05 cm) O.D. and the larger tube is 15 gauge, about 0.073 inch (0.185 cm) O.D.

For aspirating the fluid from the blind chamber 15 a 1 cc syringe with a 25 gauge Huber point needle has been used. An appropriately sized syringe fitted with a 20 gauge Huber point needle has been used for infusion and aspiration. The overall dimensions of the septum/manifold of FIG. 3, in one exemplary form, were 0.94 inch (2.38 cm) by 1.75 inches (4.45 cm).

Orientation of the system in use is variable. Accordingly, any references to upper, lower, top, bottom, vertical, etc. relate only to the orientation shown in the drawings.

It is apparent that many modifications and variations of this invention as hereinbefore set forth may be made without departing from the spirit and scope thereof. The specific embodiments described are given by way of example only and the invention is limited only by the terms of the appended claims.

We claim:

1. A bi-directional, anti-reflux vascular access system comprising:
    (A) an implantable septum/manifold comprising:
        (1) a housing;
        (2) a pair of manifold chambers within said housing;
        (3) first entry means to said chambers,
        (4) a self-sealing septum closing the first entry means to each of said chambers, and
        (5) separate second entry means to each of said chambers, and
    (B) an implantable catheter joined to said septum/manifold and comprising:
        (1) an inner collapsible flexible tube closed at the distal end, and
        (2) an outer flexible tube of substantially the same length as the inner tube closely embracing the outer wall of the inner tube,
            (a) said outer tube being open at both ends,
            (b) the inside wall of said outer tube normally engaging the outside wall of the inner tube in a separate non-adherent relationship over a substantial portion of the circumference of the inner tube, forming a normally closed passage between the tubes, and
            (c) the inner and outer tubes being joined together longitudinally over a small portion of the circumference of the inner tube,
the inside tube of said catheter being in direct fluid communication with the second entry means of one of said chambers, and the normally closed passage between the tubes being in direct fluid communication with the second entry means of the other of said chambers.

2. An access system according to claim 1 wherein said chambers of the septum/manifold are disposed in vertically stacked relation sharing a common first entry means and separated by one of said septa.

3. An access system according to claim 1 wherein said chambers of the septum/manifold are disposed in closely spaced apart side-by-side relation and have separate spaced apart first entry means.

4. An access system according to claim 1 wherein said passage formed between the closely embracing nonadherent wall portions of the tubes extends around about 50 to 95% of the circumference of the inner tube.

5. An access system according to claim 1 wherein:
 (A) the closed distal end of the inner tube is pinched together and the inside wall surfaces are laminated to each other, and
 (B) the end of the catheter is cut at an oblique angle with the laminated side forming the distal-most edge of the bevel.

6. An implantable bi-directional, anti-reflux catheter comprising:
 (A) an inner collapsible flexible tube closed at the distal end, and
 (B) an outer flexible tube of substantially the same length as the inner tube closely embracing the outer wall of the inner tube,
  (1) said outer tube being open at both ends,
  (2) the inside wall of said outer tube normally engaging the outside wall of the inner tube in a separate non-adherent relationship over a substantial portion of the circumference of the inner tube, thereby forming a normally closed passage between the tubes, and
  (3) the inner and outer tubes being joined together longitudinally over a small portion of the circumference of the inner tube.

7. A catheter according to claim 6 wherein said passage formed between the closely embracing non-adherent portions of the tubes extends around about 50 to 95% of the circumference of the inner tube.

8. An implantable septum/manifold comprising:
 (A) a housing having a central cylindrical passage in its lower portion and a connecting central passage of smaller diameter through its top wall,
 (B) a cup-like plug in the bottom end of said central passage, said plug having a cylindrical recess in its upper surface forming a manifold chamber,
 (C) a first entry means to said manifold chamber and a self-sealing resilient septum seated on the upper surface of the cup-like plug and closing the entry means,
 (D) a tightly fitted cylindrical collar seated upon said septum, the passage within said collar forming a further manifold chamber,
 (E) a first entry means to said further manifold chamber and a further self-sealing septum disposed between the top surface of said collar and the inside top wall of the housing closing said entry means, and
 (F) separate second entry means to each of said chambers,
said housing, plug and collar being formed from a rigid, inert, non-toxic, bio-compatible material for implantation in a living body.

9. An implantable bi-directional, anti-reflux catheter comprising:
 (A) an inner collapsible flexible tube closed at the distal end by being pinched together with the inside wall surfaces laminated to each other, and
 (B) an outer flexible tube of substantially the same length as the inner tube closely embracing the outer wall of the inner tube,
  (1) said outer tube being open at both ends,
  (2) the inside wall of said outer tube normally engaging the outside wall of the inner tube in a separate non-adherent relationship over a substantial portion of about 50 to 95% of the circumference of the inner tube, thereby forming a normally closed passage between the tubes,
  (3) the inner and outer tubes being joined together longitudinally over a small portion of about 5 to 50% of the circumference of the inner tube, and
  (4) the end of the catheter being cut at an oblique angle with the laminated closed distal end of the inner tube forming the distal-most edge of the bevel.

10. An implantable septum/manifold comprising:
 (A) a rigid housing formed from an inert non-toxic, biocompatible aterial for implantation in a living body,
 (B) a pair of separate closed end cylindrical manifold chambers recessed within the same surface of said housing and disposed in closely laterally spaced apart side-by-side relation,
 (C) separate spaced apart first entry means to said chambers in the form of the open ends of said chambers,
 (D) a separate septum closing the first entry means to each of said chambers, each comprising a disc of self-sealing resilient inert, non-toxic, biocompatible material of diameter greater than the diameter of the chamber and seated in an annular recess adjacent the open end of the chamber,
 (E) separate second entry means to each of said chambers in the form of passages within the housing entering the chambers adjacent to the closed ends thereof, and adapted to communicate with a single common passage int a catheter, and
 (F) means for securing the septum/manifold in place when implanted.

* * * * *

UNITED STATES PATENT AND TRADEMARK OFFICE
CERTIFICATE OF CORRECTION

PATENT NO. : 4,705,501

DATED : November 10, 1987

INVENTOR(S) : Bruce D. Wigness et al

It is certified that error appears in the above-identified patent and that said Letters Patent is hereby corrected as shown below:

Column 4, line 48, "performed" should be --preformed--.

Column 8, line 38, "aterial" should be --material--.

Column 8, line 57, "int" should be --into--.

Signed and Sealed this

Fifth Day of April, 1988

Attest:

DONALD J. QUIGG

Attesting Officer

Commissioner of Patents and Trademarks